US012736134B2

(12) United States Patent
Wright et al.

(10) Patent No.: US 12,736,134 B2
(45) Date of Patent: Sep. 15, 2026

(54) SEALING SYSTEM FOR COMPONENTS OF A GAS ANALYZER

(71) Applicant: INFICON, Inc., East Syracuse, NY (US)

(72) Inventors: Kenneth Charles Wright, Fayetteville, NY (US); Jaime Lynne Winfield, Canastota, NY (US)

(73) Assignee: INFICON, INC., East Syracuse, NY (US)

( * ) Notice: Subject to any disclaimer, the term of this patent is extended or adjusted under 35 U.S.C. 154(b) by 22 days.

(21) Appl. No.: 18/285,927

(22) PCT Filed: Apr. 7, 2022

(86) PCT No.: PCT/US2022/023872
§ 371 (c)(1),
(2) Date: Oct. 6, 2023

(87) PCT Pub. No.: WO2022/216954
PCT Pub. Date: Oct. 13, 2022

(65) Prior Publication Data

US 2024/0183446 A1 Jun. 6, 2024

Related U.S. Application Data

(60) Provisional application No. 63/172,338, filed on Apr. 8, 2021.

(51) Int. Cl.

| | |
|---|---|
| ***F16J 15/10*** | (2006.01) |
| ***F16J 15/00*** | (2006.01) |
| ***G01N 33/00*** | (2006.01) |

(52) U.S. Cl.
CPC ........... *F16J 15/102* (2013.01); *F16J 15/004* (2013.01); *F16J 15/106* (2013.01); *G01N 33/0009* (2013.01)

(58) Field of Classification Search
CPC ........ F16J 15/004; F16J 15/006; F16J 15/102; F16J 15/106; F16J 15/40; G01N 33/0009
See application file for complete search history.

(56) References Cited

U.S. PATENT DOCUMENTS 3,144,035 A * 8/1964 Hablanian .............. F16L 23/00 417/208
3,398,505 A 8/1968 Llewellyn
(Continued)

FOREIGN PATENT DOCUMENTS

EP 2334958 B1 5/2017
JP S63103954 A 5/1988
(Continued)

OTHER PUBLICATIONS

The International Bureau of WIPO, International Preliminary Report on Patentability (IPRP) and Written Opinion WO) from International Application No. PCT/US2022/023872, mailed 10-19-202 (total 6 pages.).

(Continued)

*Primary Examiner* — Christine M Mills
*Assistant Examiner* — L. Susmitha Koneru
(74) *Attorney, Agent, or Firm* — Barclay Damon LLP

(57) ABSTRACT

A sealing system includes a first seal, a second seal spaced apart from the first seal and a sealing chamber defined between the first and second seals. The sealing chamber is fluidly connected to a vacuum source. In operation, the sealing chamber is maintained at a pressure that is below atmospheric pressure. Contaminants that breach one of the first and second seals are pulled into the sealing chamber and removed by the vacuum source.

20 Claims, 17 Drawing Sheets

(56) References Cited

U.S. PATENT DOCUMENTS

| | | | | | |
|---|---|---|---|---|---|
| 3,421,292 | A | | 1/1969 | Llewellyn | |
| 3,544,118 | A | * | 12/1970 | Klein | F16J 15/006 277/927 |
| 4,322,964 | A | | 4/1982 | Melgaard et al. | |
| 4,408,765 | A | * | 10/1983 | Adelmann, Jr. | F16J 15/006 277/408 |
| 2003/0182988 | A1 | | 10/2003 | Aldridge et al. | |
| 2004/0115100 | A1 | | 6/2004 | Van Den Brink et al. | |
| 2008/0237996 | A1 | * | 10/2008 | Busold | F16J 15/54 277/400 |

FOREIGN PATENT DOCUMENTS

| | | | |
|---|---|---|---|
| TW | 200610573 | A | 4/2006 |
| TW | 201545798 | A | 12/2015 |

OTHER PUBLICATIONS

United States Patent and Trademark Office as ISA/US, International Search Report and Written Opinion (ISR/WO) from International Patent Appl. No. PCT/US22/23872, mailed Jun. 24, 2022 (7 pgs.).
European Patent Office; European Application No. 22785460.1; Dated: Feb. 2, 2025; 11 pages.
Taiwan Patent Office; First Office Action; Dated: Oct. 7, 2025; 16 pages (English version provided).
Japanese Patent Office; Notice of Reasons for Rejection; Japanese Patent Application No. 2023-561649; Dated: Jan. 6, 2026; 16 pages (English version provided).
Taiwanese Patent Office; Second Office Action: Application No. 111113194; Dated: Mar. 9, 2026; 26 pages.

* cited by examiner

SEALING SYSTEM FOR COMPONENTS OF A GAS ANALYZER

CROSS-REFERENCE TO RELATED APPLICATIONS/PRIORITY CLAIM

This application is a national stage application pursuant to 35 U.S.C. § 371 of International Application No. PCT/US2022/023872, filed on Apr. 7, 2022, which claims priority to, and the benefit of, U.S. Provisional Patent Application Ser. No. 63/172,338, filed Apr. 8, 2021, and entitled "SEALING SYSTEM FOR COMPONENTS OF A GAS ANALYZER", the entirety of which is incorporated herein by reference.

TECHNOLOGICAL FIELD

This disclosure is generally related to a sealing system for components attached to a vacuum chamber.

BACKGROUND

Gas analyzer systems are used to sample and analyze gases emitted during manufacturing processes in a variety of industries. For example, gas analyzers may be used to analyze gases produced during a semiconductor manufacturing process. Many gas analyzers operate under low pressure or vacuum conditions and require vacuum seals around valves and sensors. These seals are prone to leakage due to defects in the sealing surfaces, defects in the sealing components such as gaskets, improper installation, and gas permeation if non-metal seals are used. Leaks may also develop over time as a result of mechanical stresses and/or degradation of the sealing components due to interaction with process chemicals. Inlet components are particularly vulnerable to leaks because the inlet components interface with the device being tested or a process tool. These leaks compromise the samples taken by the gas analyzer and the ultimate monitoring of the semiconductor manufacturing process.

In some gas analyzers the vacuum seals are welded to produce a robust seal or metal seals, such as conflat seals, are used in order to attain the vacuum conditions required for the gas analyzer. These types of seals are more expensive and add excess weight to the gas analyzer system.

These are just some of the problems associated with the seal systems currently used in gas analyzers.

BRIEF SUMMARY

In an embodiment, the sealing system may comprise an inner seal that surrounds a conduit or connection of a component to the vacuum chamber. An outer seal is positioned around the inner seal and spaced apart from the inner seal with a volume, such as an inner volume or pump chamber, defined therebetween. The pump chamber may be evacuated or pumped down to a pressure that is significantly lower than atmospheric pressure. If there is a leak in the inner seal, then it will only leak gas from the inter-seal volume which is maintained at low pressure, rather than from a high pressure (e.g. 1 atm.). This would reduce the amount of gas leaking into the system by many orders of magnitude. As a result, what would normally have been a serious leak is now so small that it does not affect performance of the instrument and has no negative impact on the equipment being tested with the gas analyzer. In addition, should there be a leak in the inner seal, any toxic or otherwise volatile gases would be pumped away through the pump chamber and not released into the outside environment.

In an embodiment, the pump chamber is in connection with a double sealed turbomolecular (turbo) pump. The vacuum manifold which holds the sensor (most commonly a mass spectrometer) has a sampling interface attached and may have channels machined into it that connect the pumping volume to the lower stages of the turbo. In an embodiment, the pump chamber may be coupled to the turbo through one or more vacuum conduits integrated into the vacuum manifold. In another embodiment, the pump chamber may be coupled to the turbo through one or more vacuum conduits that are exterior to the vacuum manifold. In still another embodiment, the pump chamber may be coupled to and evacuated by a separate vacuum pump positioned external to the system or vacuum manifold.

In an embodiment, a sealing system for components of a gas analyzer includes an inner sealing member, an outer sealing member spaced apart from the inner sealing member, a sealing chamber defined between the inner and outer sealing members, and one or more conduits configured to fluidly connect the sealing chamber to a vacuum source. In operation, the sealing chamber is maintained at a pressure that is below atmospheric pressure. Contaminants that breach one of the inner and outer sealing members are pulled into the sealing chamber and removed via the one or more conduits.

In an embodiment, the inner sealing member surrounds a passage between two components of the gas analyzer. In an embodiment, at least one of the inner sealing member and the outer sealing member is comprised of an elastomeric material. In an embodiment, at least one of the inner sealing member and the outer sealing member are comprised of a polymeric material. In an embodiment, the outer sealing member is at least partially positioned within a groove defined in a surface of the gas analyzer. In a further embodiment, the one or more conduits are formed as part of the gas analyzer.

Another embodiment of a sealing system includes a first seal, a seal spaced apart from the first seal, and a sealing chamber defined between the first and second seals. The sealing chamber is fluidly connected to a vacuum source, and in operation, the sealing chamber is maintained at a pressure that is below atmospheric pressure. Contaminants that breach one of the first and second seals are pulled into the sealing chamber and removed by the vacuum source.

In an embodiment, the first seal is configured to surround a passage between two components of the gas analyzer. In an embodiment, at least one of the first and second seals is comprised of an elastomeric material. In an embodiment, at least one of the first and second seals is comprised of a polymeric material. In a further embodiment, the second seal is at least partially positioned within a groove defined in a surface of the gas analyzer. In an embodiment, the sealing chamber is fluidly coupled to the vacuum source using one or more conduits that are formed as part of the gas analyzer. In an embodiment, the vacuum source is positioned away from the gas analyzer. In an embodiment, the vacuum source is a system vacuum pump for the gas analyzer.

An embodiment of sealing a junction between components of a gas analyzer includes structuring a sealing system between the components to include a first seal, a seal spaced apart from the first seal, and a sealing chamber defined between the first and second seals. The scaling chamber is fluidly connected to a vacuum source which maintains the sealing chamber at a pressure that is below atmospheric pressure when in operation. Contaminants that breach one of the first and second seals and are pulled into the sealing chamber and removed using the vacuum source.

The sealing system and methods disclosed herein may be used to replace heavy and more expensive metal sealing technology (e.g. conflat flanges) since the disclosed sealing system and methods are easier to use and may employ lighter and cheaper elastomer or polymer seals. This sealing system may still provide ultrahigh vacuum seals that are robust against leaks. While the examples of the sealing system disclosed herein are focused on valves and inlet components, embodiments of the sealing system are also compatible and may be used with any component that is to be attached to the vacuum chamber of a gas analyzer such as gauges, sensors, and the like.

BRIEF DESCRIPTION OF DRAWINGS

A more particular description of the invention briefly summarized above may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. Thus, for further understanding of the nature and objects of the invention, references can be made to the following detailed description, read in connection with the drawings in which.

The attached drawings are for purposes of illustration and are not necessarily to scale.

DETAILED DESCRIPTION

The following discussion relates to various embodiments of a sealing system for components coupled to a gas analyzer. It will be understood that the herein described versions are examples that embody certain inventive concepts as detailed herein. To that end, other variations and modifications will be readily apparent to those of sufficient skill. In addition, certain terms are used throughout this discussion in order to provide a suitable frame of reference with regard to the accompanying drawings. These terms such as "upper", "lower", "forward", "rearward", "interior", "exterior", "front", "back", "top", "bottom", "inner", "outer", "first", "second", and the like are not intended to limit these concepts, except where so specifically indicated. The terms "about", "approximately", or "substantially" as used herein may refer to a range of 80%-125% of the claimed or disclosed value unless otherwise stated. With regard to the drawings, their purpose is to depict salient features of the sealing system for components coupled to a gas analyzer and are not specifically provided to scale.

Figure 1A:
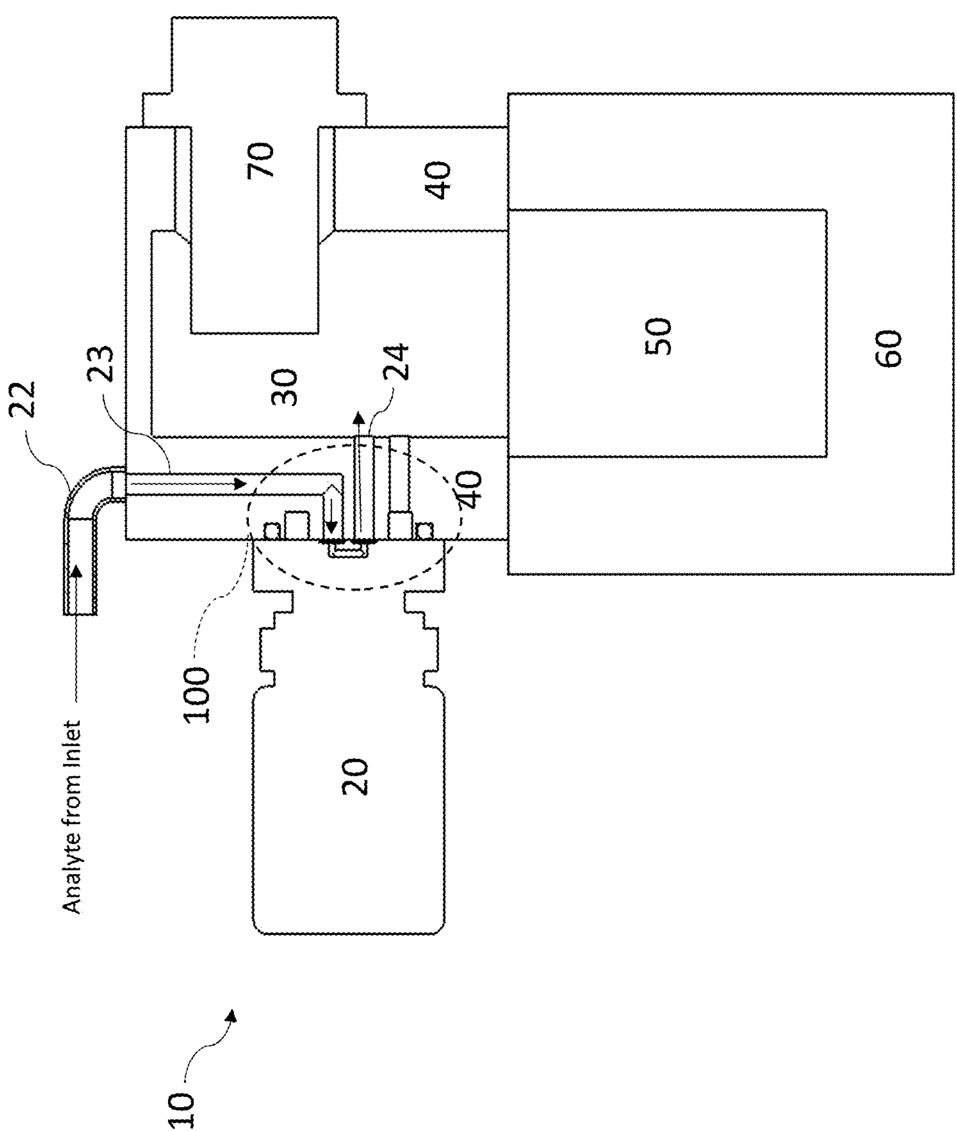
FIG. 1A illustrates a schematic cross sectional view of an embodiment of a portion of a gas analyzer with an embodiment of a sealing system.
Figure 1B:
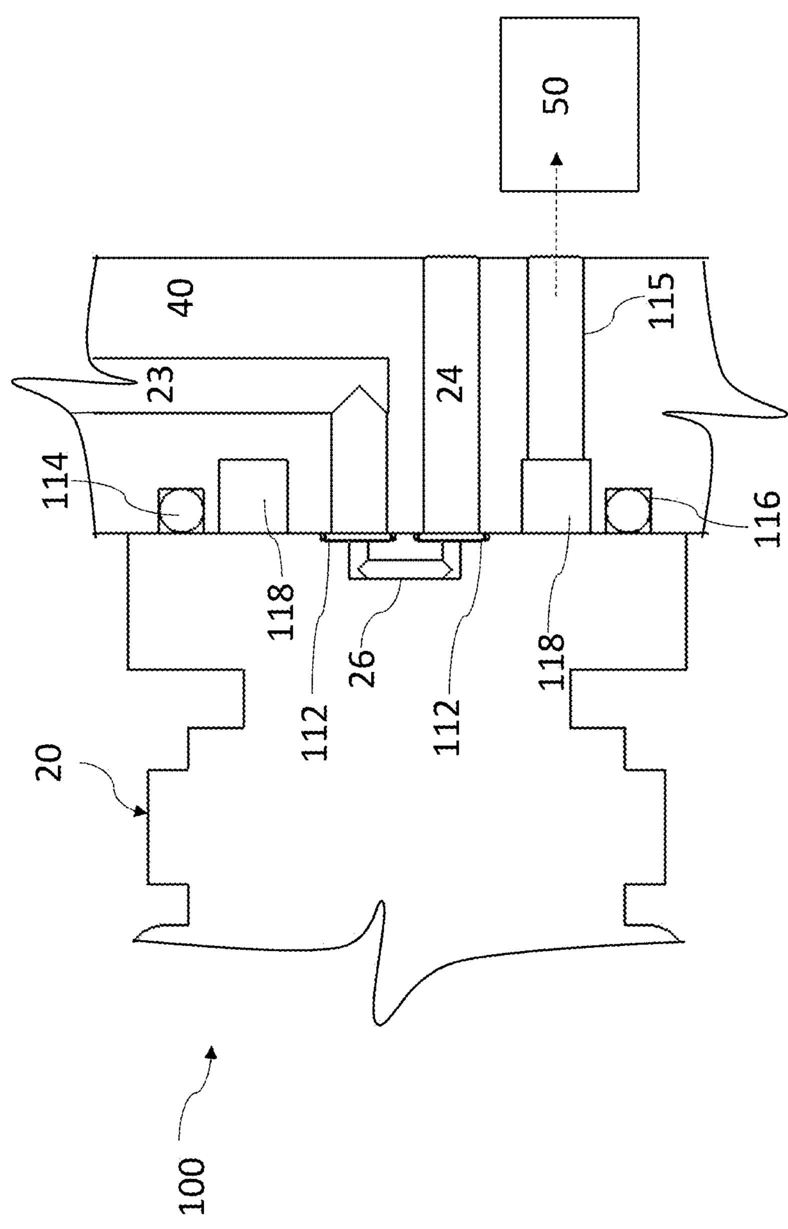
FIG. 1B illustrates a close-up of the embodiment of the sealing system from FIG. 1A.
Figure 2:
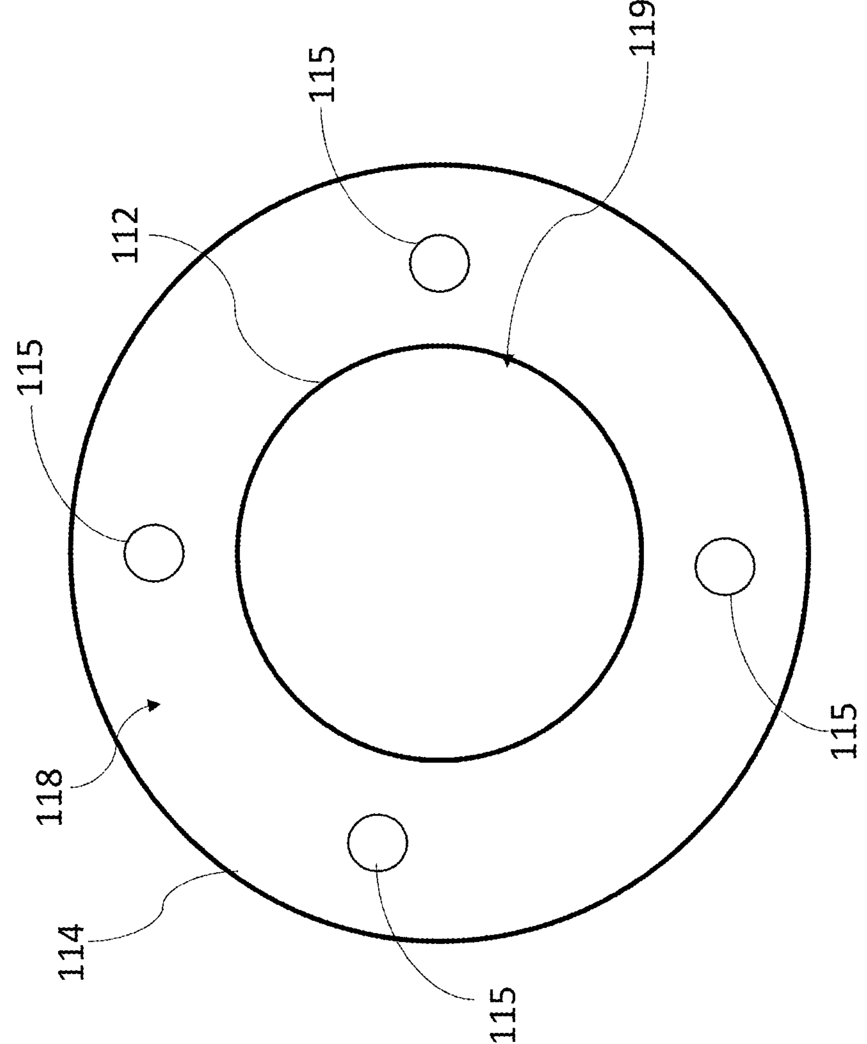
FIG. 2 illustrates a close up schematic depiction of an opening to a valve being sealed by an embodiment of the sealing system.

A portion of a gas analyzer 10 is shown in FIGS. 1A-2. The gas analyzer 10 generally comprises a valve 20 coupled to a housing 40 surrounding a vacuum chamber 30. The valve 20 comprises an inlet 23 and an outlet 24. One or more interior conduits 26 are fluidly connected to the inlet 23 and the outlet 24, and the outlet 24 is fluidly connected to the vacuum chamber 30. As shown in FIG. 1A, the inlet 23 may be fluidly coupled to additional exterior or supplemental inlet channels 22. A sensor 70 may be coupled to the vacuum chamber housing 40 and configured to detect gases within the vacuum chamber 30. In an embodiment, the sensor 70 may be a mass spectrometer. A system vacuum pump 50 is surrounded by a vacuum manifold 60 and is configured to pump down the vacuum chamber 30 to a desired pressure level. As shown, a sealing system 100 is used to seal the connection between the valve 20 and the vacuum chamber 30 in order to prevent leaks, which would compromise the function of the valve 20 and/or the monitored process.

Referring to FIGS. 1B and 2, the sealing system 100 includes a first seal and a second seal. As shown, the sealing system has an inner seal 112 or inner sealing member defining an opening 119 that is configured to accept or surround a channel or conduit and is positioned around the circumference of the channel or conduit, such as the inlet 23 or the outlet 24 of the valve 20. An outer seal 114 or outer sealing member is positioned around and spaced away from the inner seal 112 such that an inner volume or seal chamber 118 is defined between the inner seal 112 and the outer seal 114. In some embodiments, including the embodiments shown in FIGS. 1A, 1B, 5-7B, 9A, 10A, and 10B, the outer seal 114 may be positioned at least partially in a groove 116 that is formed in the valve 20 or in the housing 40 of the vacuum chamber 30. In some embodiments, the outer seal 114 may be an O-ring comprised of an elastomeric or polymer material. In the embodiment shown schematically in FIGS. 1B and 2, the seal chamber 118 is fluidly connected to a system vacuum pump 50 using one or more vacuum conduits 115. However, in some embodiments, such as the embodiment shown in FIGS. 1A and 3, the seal chamber 118 is instead fluidly connected to the vacuum chamber 30 and is pumped down as the vacuum chamber 30 is pumped down.

Figure 3:
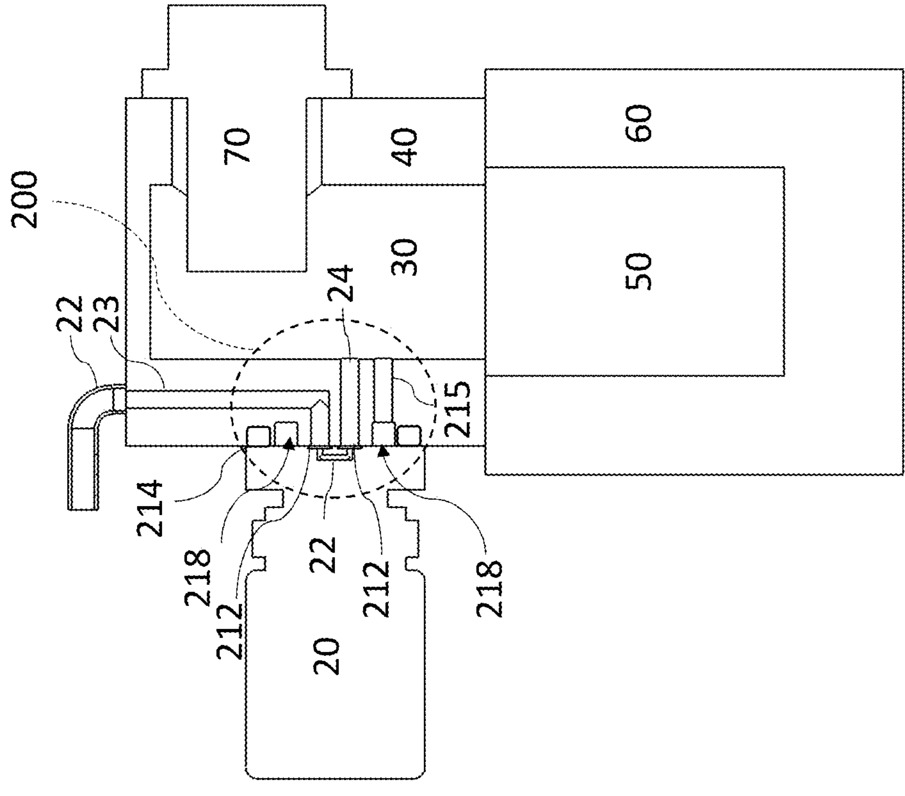
FIG. 3 illustrates a schematic cross sectional view of an embodiment of a portion of a gas analyzer with another embodiment of the sealing system.
Figure 3:
Figure 4A:
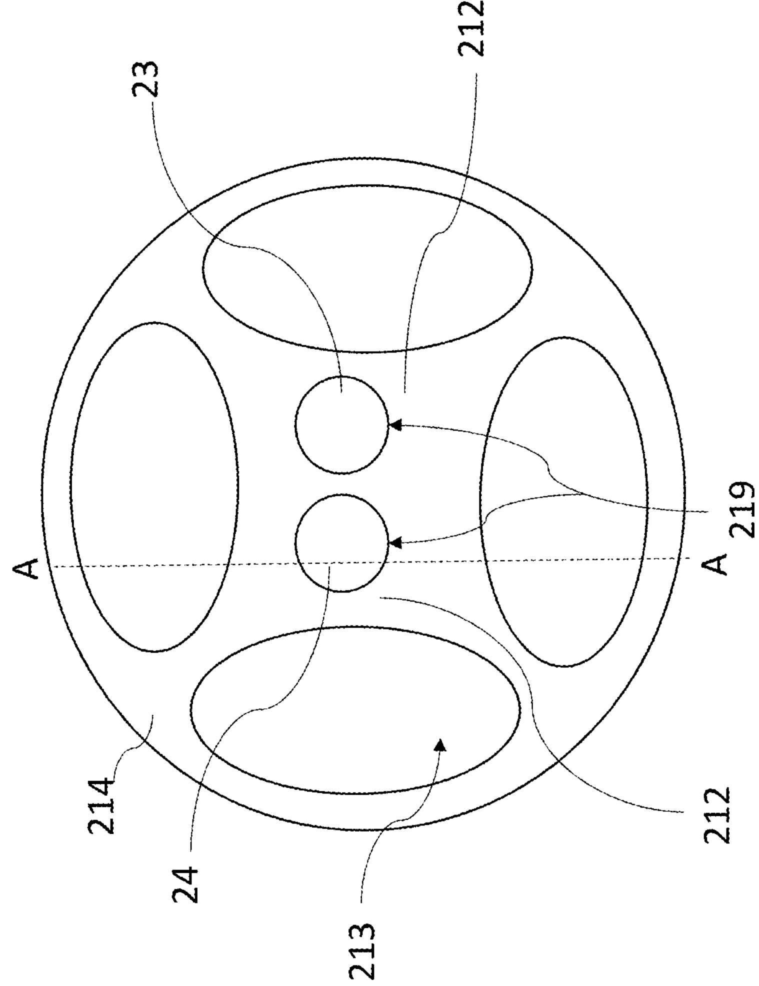
FIG. 4A illustrates a close up schematic depiction of a dual opening to a valve being sealed by an embodiment of the sealing system.
Figure 4B:
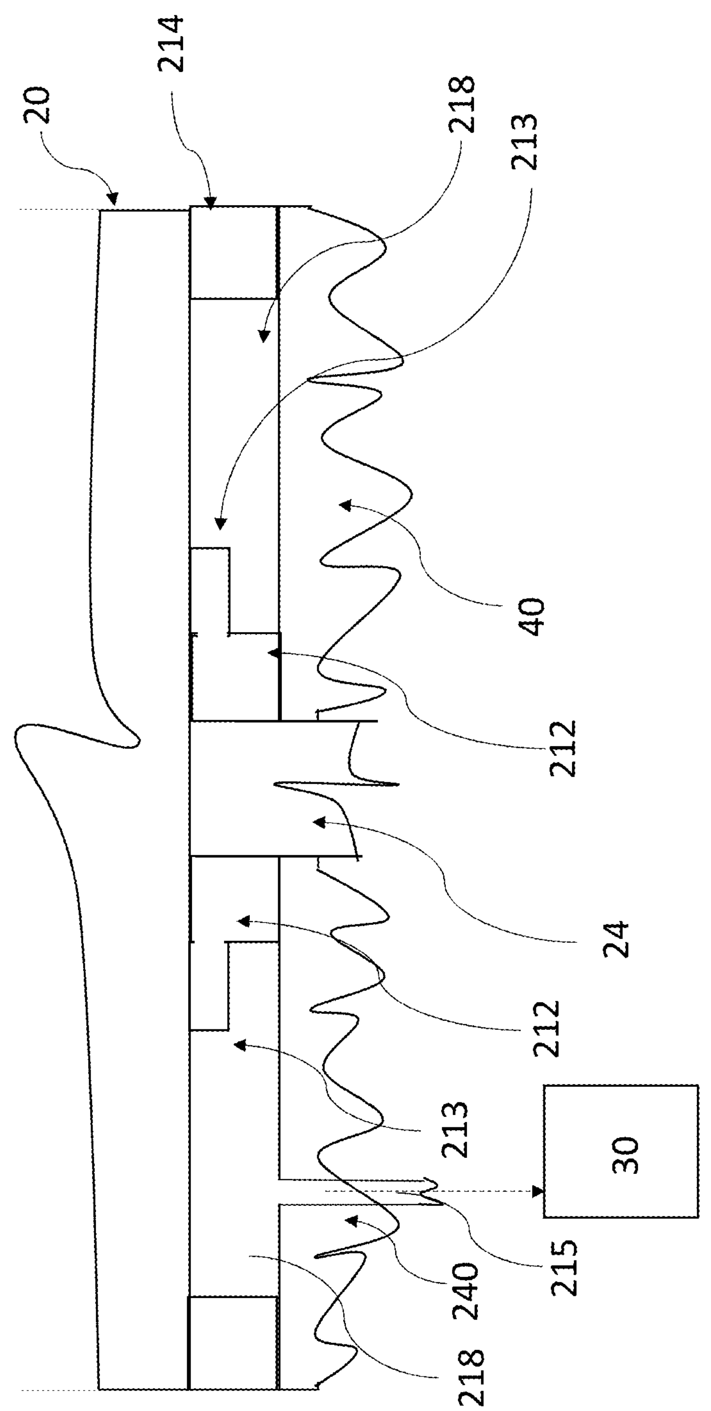
FIG. 4B illustrates a schematic cross sectional view of the embodiment of FIG. 4A along A-A.
Figure 5:
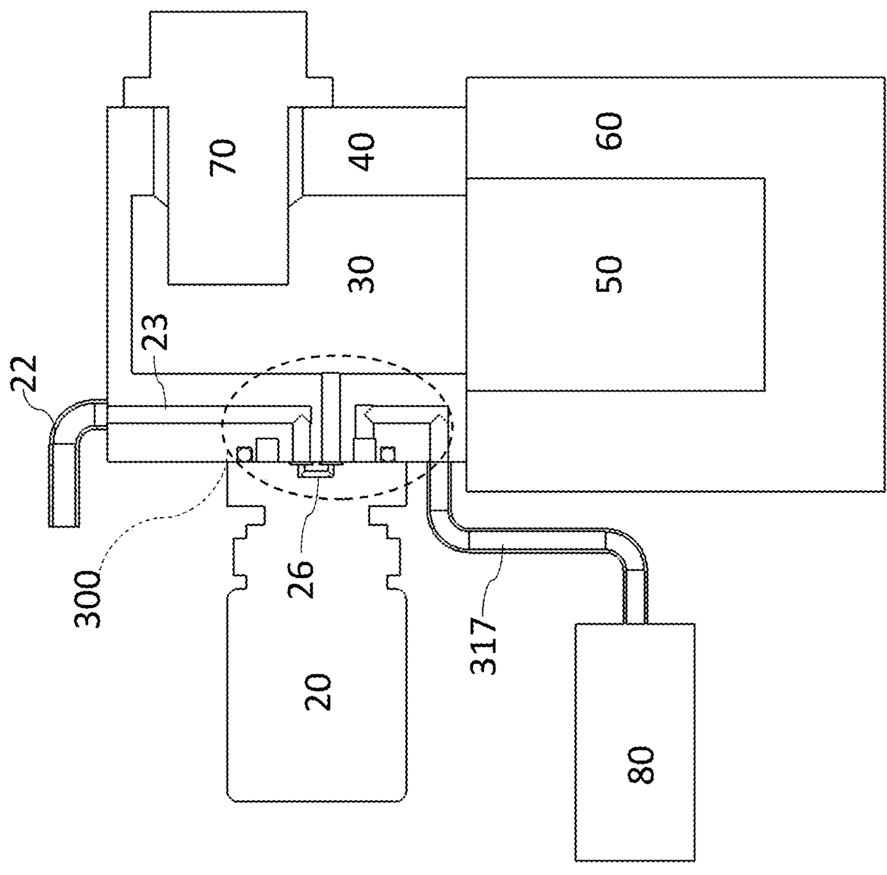
FIG. 5 illustrates a schematic cross sectional view of another embodiment of a portion of a gas analyzer comprising another embodiment of the sealing system.
Figure 5:
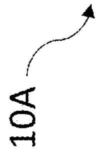
Figure 6:
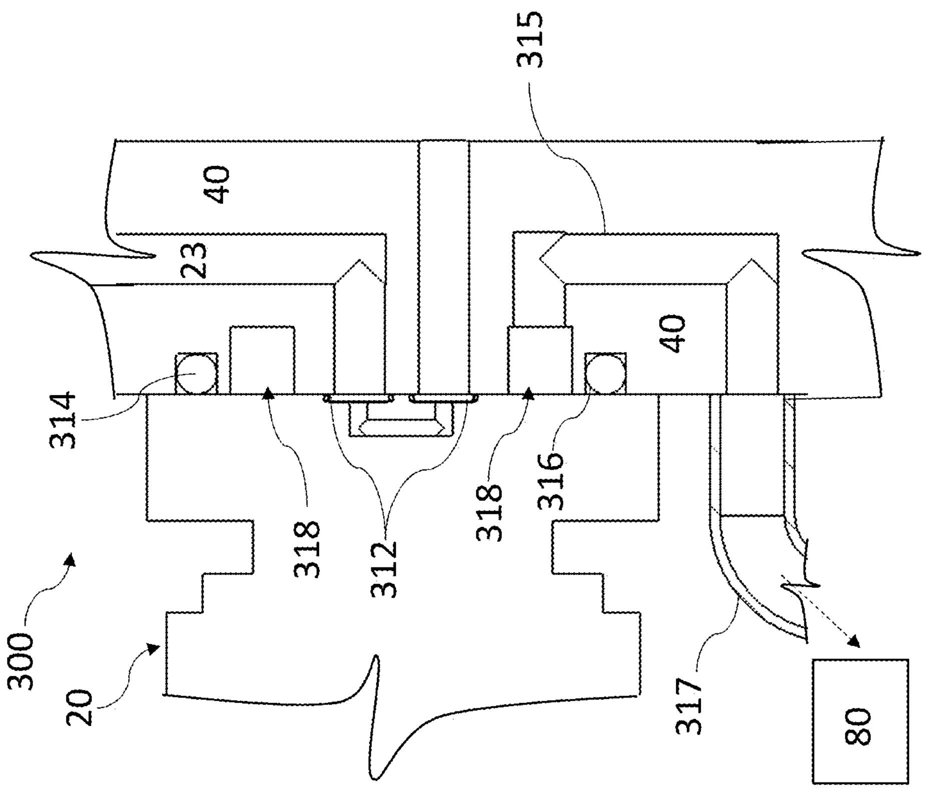
FIG. 6 illustrates a close-up view of the embodiment of the sealing system of FIG. 5.

FIGS. 3-4B illustrate a portion of a gas analyzer 10A with an embodiment of the sealing system 200 comprising at least one inner seal 212 or sealing member and an outer seal 214 or sealing member that is not positioned in a groove or channel formed in the valve 20 or the housing 40 of the vacuum chamber 30. Instead, the outer seal 214 may be positioned at the interface of the valve and the housing 40 of the vacuum chamber 30. The outer seal 214 may be a separate component from the one or more inner seals 212 or they may formed as a single component such as the embodiment illustrated in FIG. 4A. The at least one inner seal 212 defines an opening 219 configured to accept or otherwise surround a channel or conduit such as the inlet 23 or outlet 24 of the valve 20. The outer seal 214 is positioned between the valve 20 and the housing 40 of the vacuum chamber 30. Both the outer seal 214 and the at least one inner seal 212 may be comprised of the same material, such as an elastomeric or polymer material, or they may each be comprised of different materials. Although many of the embodiments of the outer and inner seals and the conduits are shown as being an oval (such as a circle) or an ellipse, one skilled in the art would realize that other shapes are possible for these components. FIG. 4B is a schematic cross section taken along line A-A of FIG. 4A. As shown, the two or more openings 213 defined between the one or more inner seals 212 and the outer seal 214 define a seal chamber 218 that extends between the outer seal 214 and the one or more inner seals 212. One or more vacuum conduits 215 fluidly connect the seal chamber 218 to the vacuum chamber 30 as in sealing system 100.

FIGS. 5-7B illustrate a portion of a gas analyzer 10A with a scaling system 300 comprising an outer seal 314 similar to that of FIGS. 1A and 1B. In this embodiment, the outer seal 314 is positioned in a groove or channel 316 formed in the valve 20 and/or in the housing 40 of the vacuum chamber 30. The seal chamber 318 is formed between the outer seal 314 and one or more inner seals 312. In this embodiment, the seal chamber 318 is fluidly connected to a vacuum conduit 315 that is integrated with or formed into the housing 40 of the vacuum chamber 30. The vacuum conduit 315 is then fluidly connected to a supplemental vacuum conduit 317 that is external to the vacuum chamber housing 40 and/or the gas analyzer 10A. As shown in FIGS. 5-7B, the supplemental vacuum conduit 317 fluidly connects to a secondary vacuum pump 80 that may be external to the gas analyzer 10A. This secondary vacuum pump 80 is separate from the system vacuum 50 that is configured to separately pump down the vacuum chamber 30. As such, the environment of the seal chamber 318 may be controlled independently from that of the vacuum chamber 30.

Figure 7A:
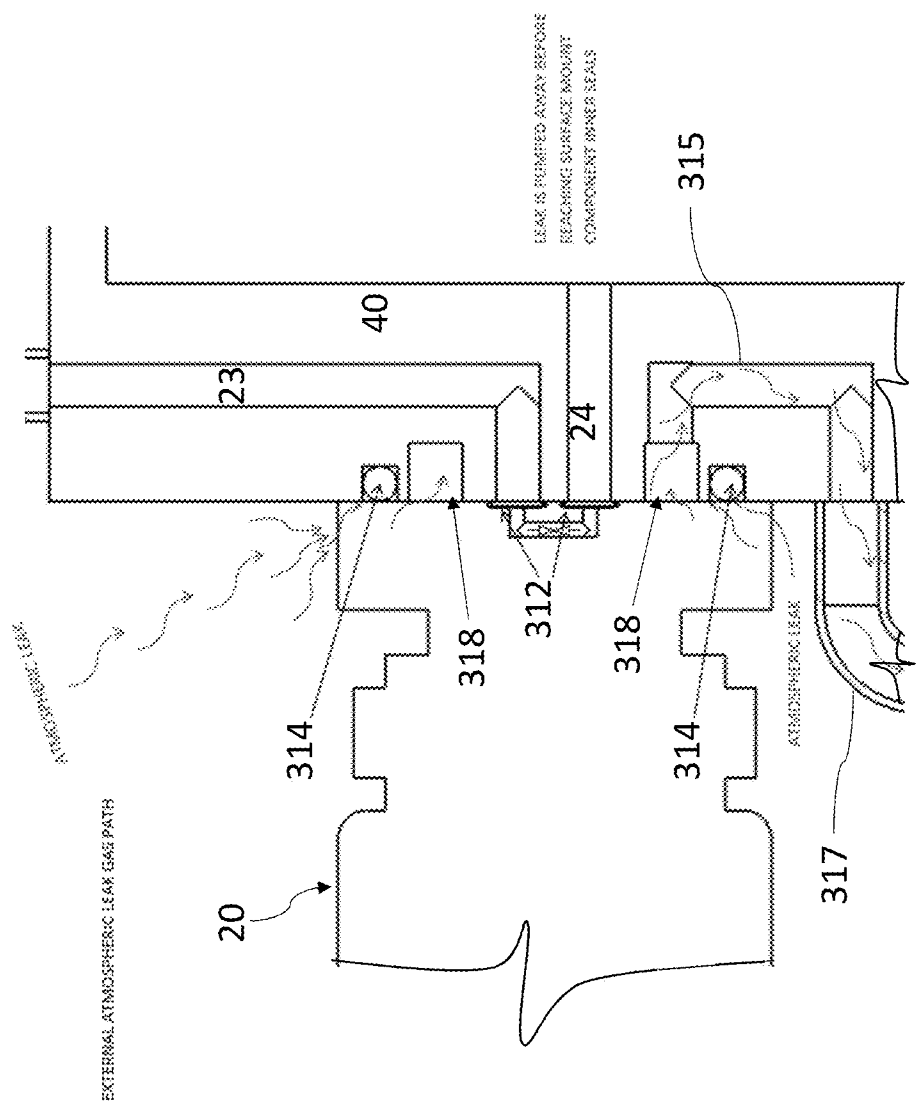
FIG. 7A illustrates an enlarged schematic cross section of the embodiment of the sealing system of FIG. 6 indicating an example of air flow at a valve interface and within a pump chamber.
Figure 7B:
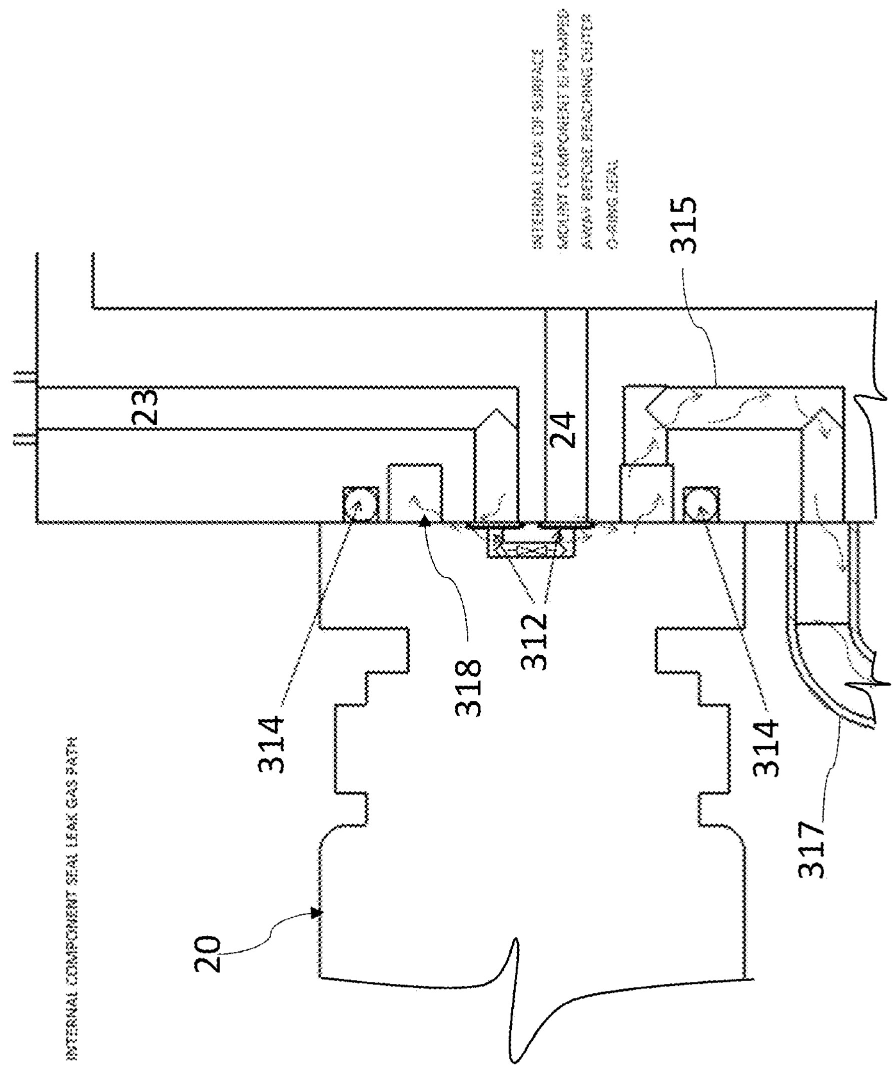
FIG. 7B illustrates an enlarged schematic cross section of the embodiment of the sealing system of FIG. 6 indicating another example of air flow at a valve interface and within a pump chamber.
Figure 8:
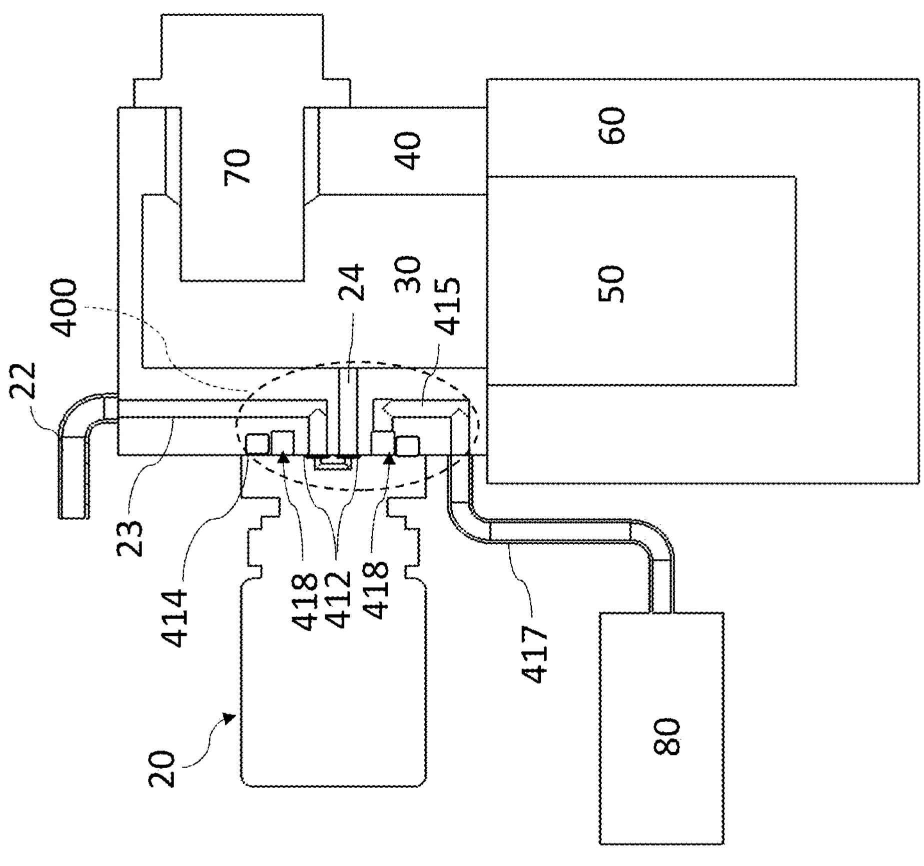
FIG. 8 illustrates a schematic cross sectional view of an embodiment of a portion of a gas analyzer with another embodiment of the sealing system.
Figure 8:
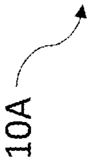

FIGS. 7A and 7B depict examples of airflow patterns through the sealing system 300. In the case of an atmospheric leak at the outer seal 314 schematically illustrated in FIG. 7A as a plurality of arrows, the atmospheric leak enters the pump chamber 318 and is evacuated through the vacuum conduits 315 (and supplemental vacuum conduit 317) by the secondary vacuum pump 80. Alternatively and as schematically illustrated in FIG. 7B as a plurality of arrows, if a leak develops in the one or more inner seals 312, any gas that escapes will enter the pump chamber 318 and be evacuated through the vacuum conduits 315 (and supplemental vacuum conduit 317). In this manner, toxic or otherwise volatile gases do not escape into the surrounding environment. As shown in FIG. 8, a portion of the gas analyzer 10A is illustrated with a sealing system 400 sealing the valve 20 against the housing 40 of the vacuum chamber 30. In this embodiment, the outer seal 414 and the one or more inner seals 412 are similar to that of FIGS. 3 and/or 4B. A seal chamber 418 is formed between the outer seal 414 and one or more inner seals 412. The seal chamber 418 is coupled to a vacuum conduit 415 that is integrated with or formed into the housing 40 of the vacuum chamber 30. The vacuum conduit 415 is fluidly connected to a supplemental vacuum conduit 417 that may be external to the vacuum chamber housing 40 and/or the gas analyzer 10A. As shown in FIG. 8, the supplemental vacuum conduit 417 fluidly connects to a secondary vacuum pump 80 that may be external from the gas analyzer 10A. This secondary vacuum pump 80 is separate from the system vacuum pump 50 that is configured to pump down the vacuum chamber 30 and as such, may be controlled independently from the system vacuum pump 50.

Figure 9A:
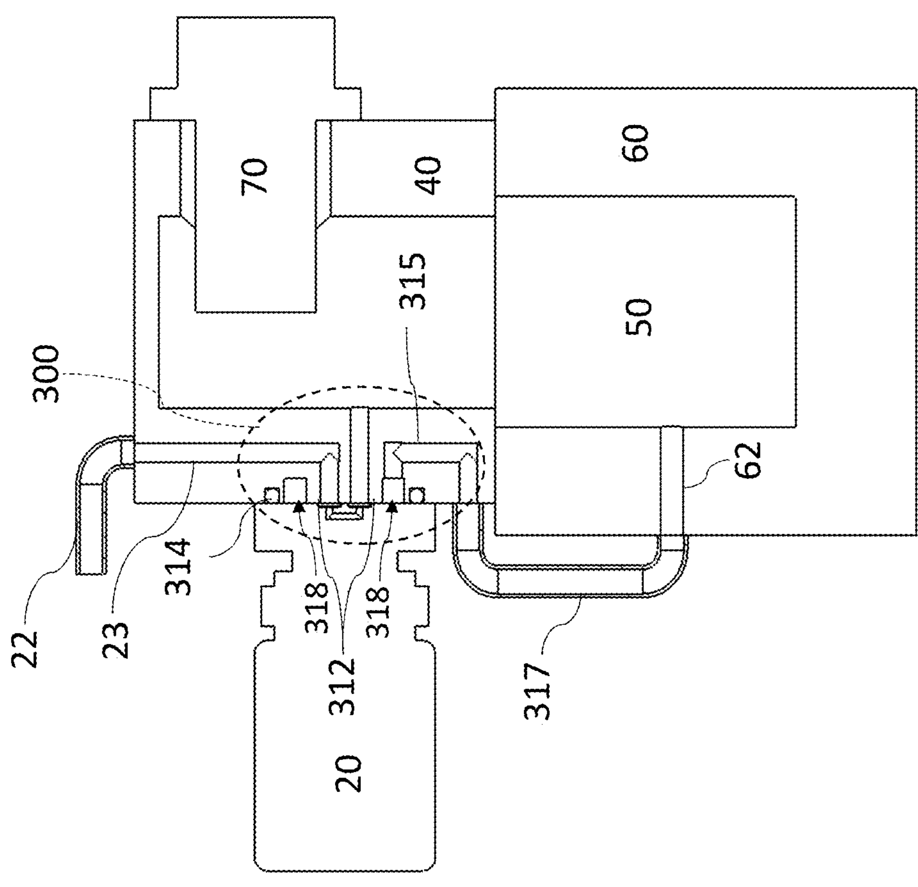
FIG. 9A illustrates a schematic cross sectional view of an embodiment of a portion of a gas analyzer with another embodiment of the sealing system.
Figure 9A:
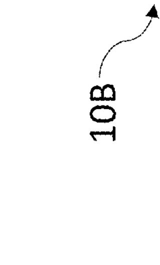

FIG. 9A illustrates a portion of a gas analyzer 10B with the embodiment of the sealing system 300 from FIGS. 5-7B that is not connected to a secondary vacuum pump 80. Here, the supplemental vacuum conduit 317 of the sealing system 300 connects the vacuum conduit 315 and therefore, the pump chamber 318 to the system vacuum pump 50 through one or more system channels 62 formed in the vacuum manifold 60. In this manner, the system vacuum pump 50 may be used to pump down or evacuate the vacuum chamber 30 and the pump chamber 318. The supplemental vacuum conduit 317 may be detachable such that the supplemental vacuum conduit 317 may be used to fluidly connect to the system vacuum pump 50 or to a secondary vacuum pump 80 as in FIGS. 5-7B. When the supplemental vacuum conduit 317 is fluidly connect to a secondary vacuum pump 80, the one or more system channels 62 may be plugged or otherwise blocked from outside contamination.

Figure 9B:
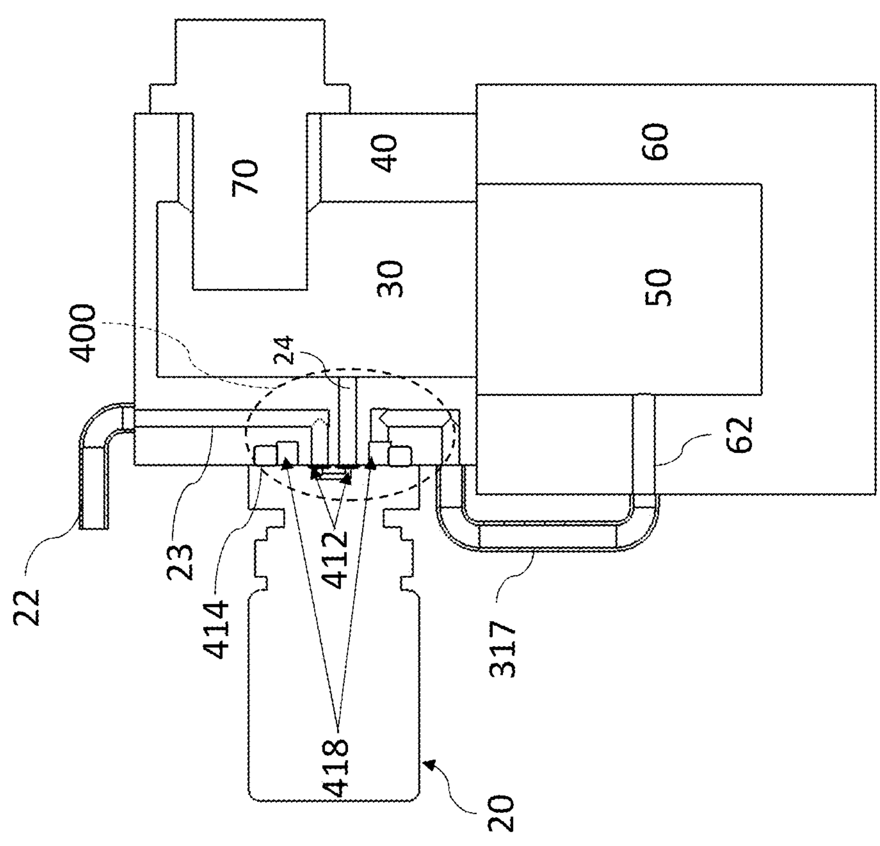
FIG. 9B illustrates a schematic cross sectional view of an embodiment of a portion of a gas analyzer with another embodiment of the sealing system.
Figure 9B:
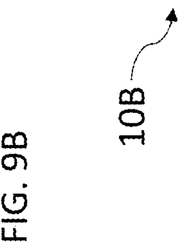

FIG. 9B shows a portion of the gas analyzer 10B with an embodiment of the sealing system 400 sealing the valve 20 against the housing 40 of the vacuum chamber 30. In this embodiment, the one or more inner seals 412 and the outer seal 416 are similar to that of FIGS. 3 and/or 4B. Accordingly, a seal chamber 418 is formed between the outer seal 414 and the one or more inner seals 412. The seal chamber 418 is coupled to a vacuum conduit 415 that is integrated with or formed into the housing 40 of the vacuum chamber 30. The vacuum conduit 415 may then fluidly connect to a supplemental vacuum conduit 417 that may be external to the vacuum chamber housing 40 and/or the gas analyzer 10A. As shown in FIG. 8, the supplemental vacuum conduit 417 fluidly connects to a secondary vacuum pump 80 that may be external from the gas analyzer 10B. This secondary vacuum pump 80 is separate from the system vacuum pump 50 that is configured to pump down the vacuum chamber 30, and as such, may be controlled independently from the system vacuum pump 50.

Figure 10A:
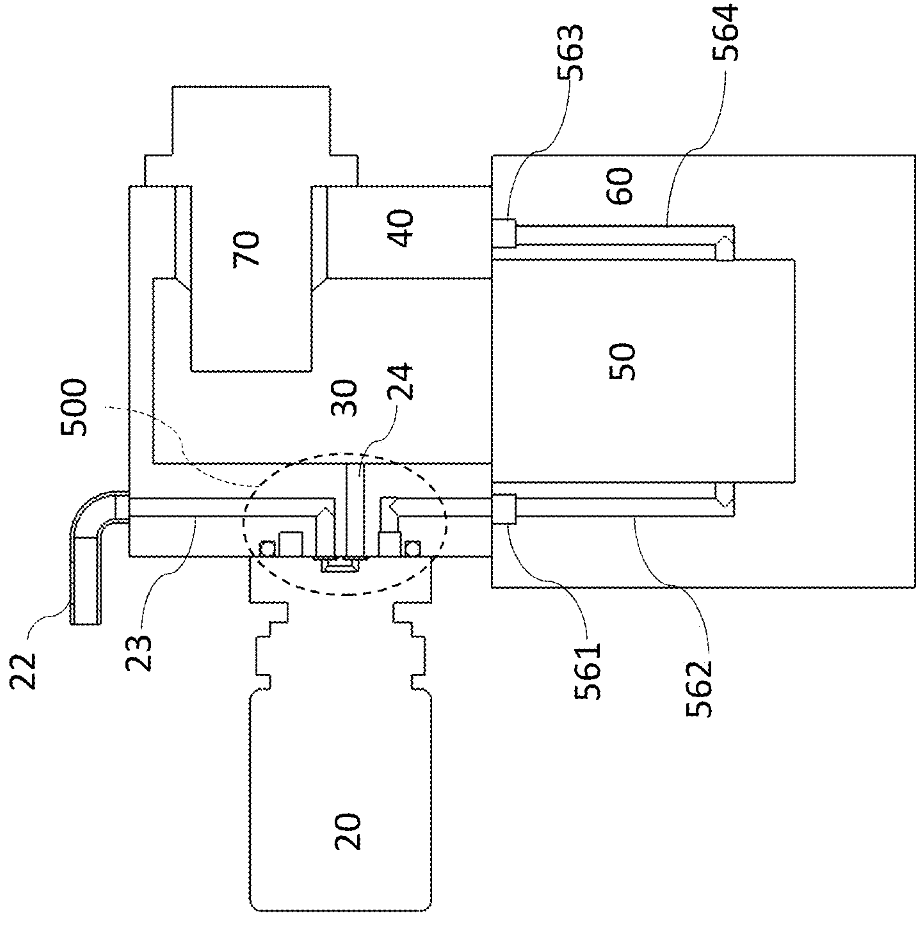
FIG. 10A illustrates a schematic cross sectional view of an embodiment of a portion of a gas analyzer with another embodiment of the sealing system.
Figure 10A:
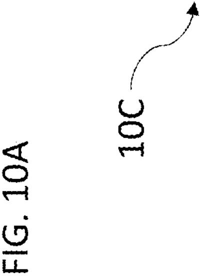
Figure 10B:
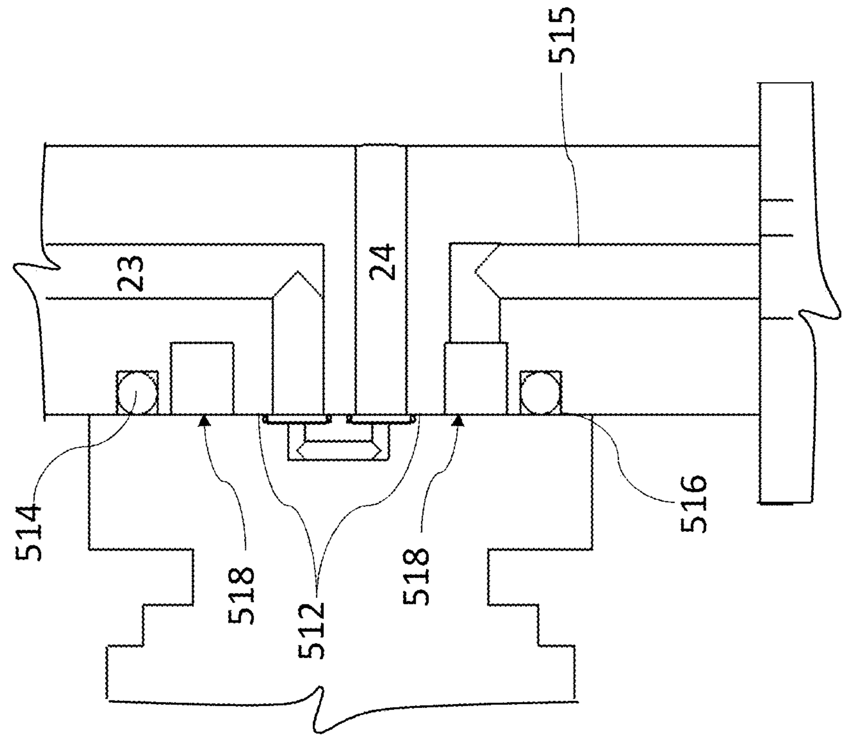
FIG. 10B illustrates a close up of a portion of the embodiment of FIG. 10A.
Figure 10B:
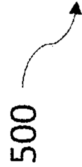

In the embodiment shown in FIGS. 10A and 10B, a portion of a gas analyzer 10C is shown with another embodiment of the sealing system 500. Here, the outer seal 514 is similar to the outer seal 114 described in FIGS. 1A-2. The outer seal 514 may be positioned at least partially within a groove or channel 516 that is formed as part of the valve 20 or housing 40 of the vacuum chamber 30. A sealing chamber 518 is defined between the outer seal 514 and the at least one inner seal 512. The sealing chamber 518 is coupled to a vacuum conduit 515 that is integrated with or formed into the housing 40 of the vacuum chamber 30. As shown particularly in FIG. 10A, the vacuum conduit 515 is coupled to one or more system conduits 562, 564 formed in or integrated into the vacuum manifold 60 that are coupled to the system vacuum pump 50. The diameter of the system conduits 562, 564 may vary according to the desired vacuum characteristics or the design of the gas analyzer. For example, a portion of the system conduit 561, 563 positioned near the vacuum chamber 30 or vacuum chamber housing 40 may have a greater diameter than the remaining portion of the system conduit 562, 564 extending to the system vacuum pump 50. Accordingly, this embodiment of the gas analyzer 10C has a sealing system 500 that comprises a sealing chamber 518 that is coupled to the system vacuum pump 50 through conduits that are integrated or formed with the vacuum manifold 60 and the housing 40 of the vacuum chamber 30.

Figure 11:
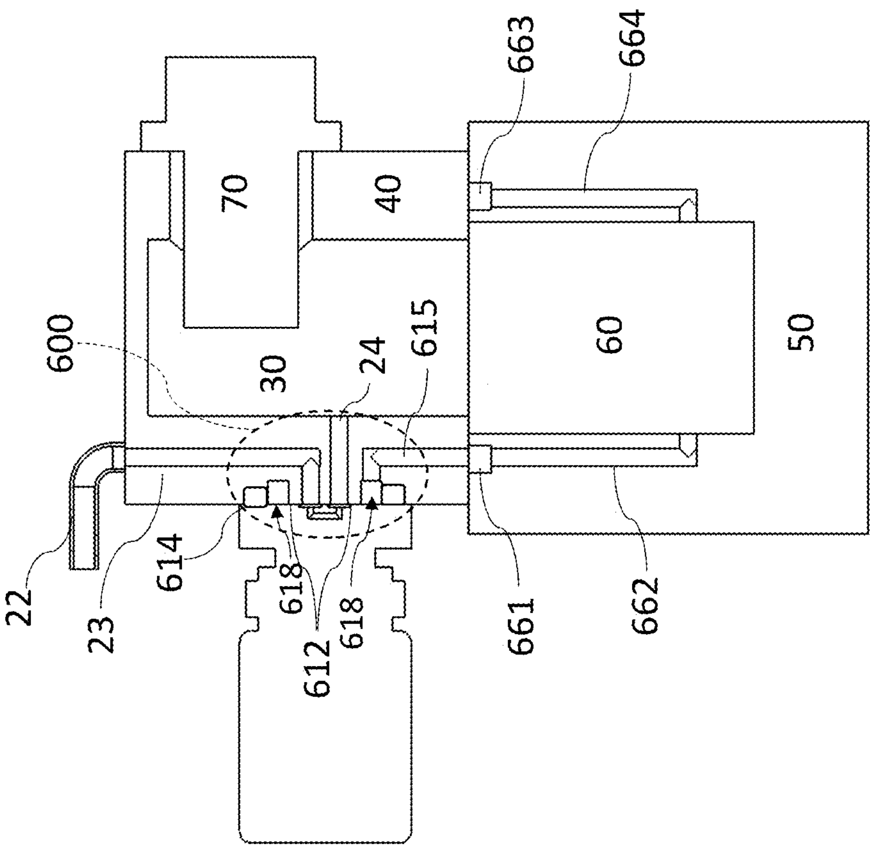
FIG. 11 illustrates a schematic cross sectional view of an embodiment of a portion of a gas analyzer with another embodiment of the sealing system.
Figure 11:

Another embodiment of the sealing system 600 is shown in FIG. 11. In this embodiment the outer seal 614 is similar to the outer seal 214 described in FIGS. 3 and 4A-4B. The outer seal 614 is positioned between or at the interface of the valve 20 and the housing 40 of the vacuum chamber 30. The at least one inner seal 612 is positioned inside the outer seal 614 and defines at least one opening configured to accept and otherwise surround a channel or conduit such as the inlet 23 or the outlet 24 of the valve 20. A sealing chamber 618 is defined between the outer seal 614 and the at least one inner seal 612. The sealing chamber 618 is fluidly connected to a vacuum conduit 615 that is integrated with or formed into the housing 40 of the vacuum chamber 30. The vacuum conduit 615 may be fluidly connected to one or more system conduits 662, 664 formed in or integrated into the vacuum manifold 60 that are fluidly connected to the system vacuum pump 50. The diameter of the system conduits 662, 664 may vary according to the desired vacuum characteristics or the design of the gas analyzer. For example, a portion of the system conduit 661, 663 positioned near the vacuum chamber 30 or vacuum chamber housing 40 may have a greater diameter than the remaining portion of the system conduit 662, 664 extending to the system vacuum pump 50. Accordingly, this embodiment of the gas analyzer 10C also has a sealing system 600 that comprises a sealing chamber 618 that is fluidly connected to the system vacuum pump 50 through conduits that are integrated or formed with the vacuum manifold 60 and the housing 40 of the vacuum chamber 30.

The one or more inner seals and the outer seals described in the foregoing description may be comprised of an elastomeric material such as rubber. The pump chambers may be pumped down to a level well below 1 atm. or 760 torr. In an embodiment, the pressure within the pump chamber may be pumped down to and maintained at less than 1 torr. In another embodiment, the pressure within the pump chamber may be pumped down to and maintained at less than 0.5 torr. While the embodiments of the sealing system 100, 200, 300, 400, 500, 600 have been described with regard to a valve 20, such embodiments of the sealing system may be used to seal any surface mount component to a vacuum chamber of a gas analyzer, such as a sensor 70.

Figure 12B:
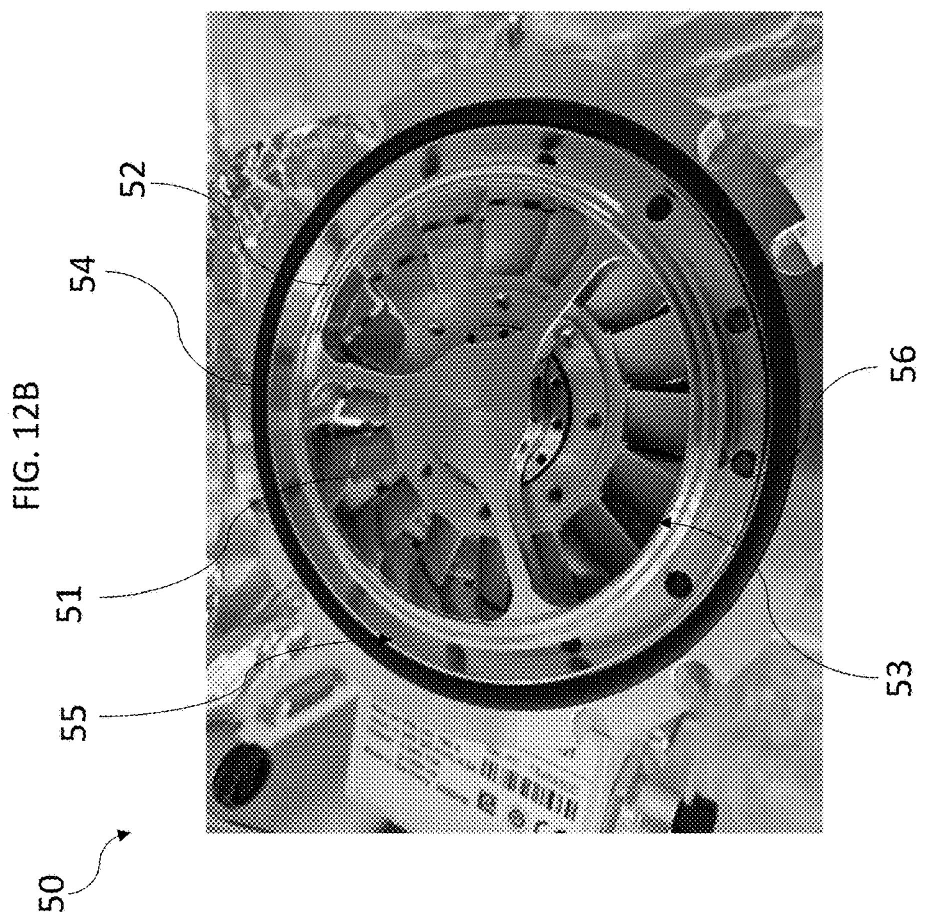
FIG. 12B illustrates a top perspective view of an embodiment of the turbo vacuum pump.
Figure 12A:
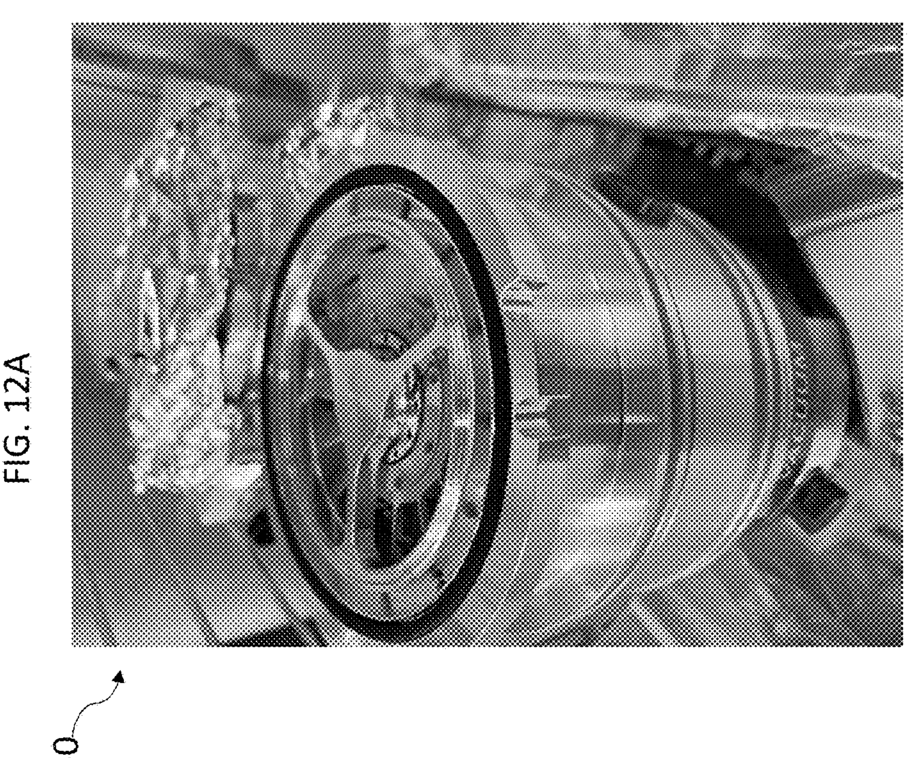
FIG. 12A illustrates a perspective view of an embodiment of a turbo vacuum pump.

The vacuum pumps used in the described embodiments may be any known vacuum pump. In an embodiment, the system vacuum pump 50, or the secondary vacuum pump 80 may be used in conjunction with a getter material located in the pump chamber. In another embodiment described with reference to FIGS. 12A and 12B, the system pump 50 may be a turbo pump comprising a plurality of blades 51 operatively coupled to an actuator and configured to rotate within a blade chamber 53. An inner seal 52 is positioned around an opening of the blade chamber 53 to seal the blade chamber against the vacuum manifold 60 or the housing 40 of the vacuum chamber 30. An outer seal 54 is positioned outside the inner seal 52 and surrounding the inner seal 52. The volume 55 defined between the seals 52, 54 may be pumped down to a level well below 1 atm. or 760 torr via one or more pump conduits 56. When a turbo pump such as the one illustrated in FIGS. 12A and 12B is used as the system vacuum pump 50, the one or more pump conduits 56 may be coupled to the pump chambers of the sealing systems in order to pump down the pump chambers. For example, the one or more pump conduits 56 may be coupled to the pump chamber via internal or integrated vacuum conduits 515, 615 and system conduits 562, 564, 662, 664 such that the sealing chamber 518, 618 of the sealing system 500, 600 the vacuum conduits 515, 615 the system conduits 562, 564, 662, 664 and the system vacuum pump 50 are all located within a manifold 60 or housing 40 of the gas analyzer 10C.

While the present invention has been particularly shown and described with reference to certain exemplary embodiments, it will be understood by one skilled in the art that various changes in detail may be effected therein without departing from the spirit and scope of the invention that can be supported by the written description and drawings. Further, where exemplary embodiments are described with reference to a certain number of elements, it will be understood that the exemplary embodiments can be practiced utilizing either less than or more than the certain number of elements.

The invention claimed is:

1. A sealing system for a gas analyzer, comprising:

an inner sealing member positioned at an interface between a valve and a housing of a vacuum chamber, wherein the valve includes an inlet and an outlet and the inner sealing member surrounds the inlet and the outlet of the valve;

an outer sealing member spaced apart from the inner sealing member positioned at the interface between the valve and the housing of a vacuum chamber;

a sealing chamber defined between the inner and outer sealing members; and one or more conduits configured to fluidly connect the sealing chamber to the vacuum chamber, wherein in operation, the sealing chamber is maintained at a pressure that is below atmospheric pressure, and wherein contaminants that breach one of the inner and outer sealing members are pulled into the sealing chamber and removed via the one or more conduits.

2. The sealing system of claim 1, wherein the inner sealing member and the outer sealing member are formed as a single component.

3. The sealing system of claim 1, wherein at least one of the inner sealing member and the outer sealing member is comprised of an elastomeric material.

4. The sealing system of claim 1, wherein at least one of the inner sealing member and the outer sealing member are comprised of a polymeric material.

5. The sealing system of claim 1, wherein the outer sealing member is at least partially positioned within a groove defined in a surface of the gas analyzer.

6. The sealing system of claim 1, wherein the one or more conduits are formed as part of the gas analyzer.

7. A sealing system comprising:

a first seal positioned at an interface between a valve and a housing of a vacuum chamber;

a second seal spaced apart from the first seal and positioned at the interface between the valve and the housing of a vacuum chamber, wherein the valve includes an inlet and an outlet and the second sealing member surrounds the inlet and the outlet of the valve; and a sealing chamber defined between the first and second seals, wherein the sealing chamber is fluidly connected to the vacuum chamber, wherein in operation, the sealing chamber is maintained at a pressure that is below atmospheric pressure, and wherein contaminants that breach one of the first and second seals are pulled into the sealing chamber and removed through the vacuum chamber.

8. The sealing system of claim 7, wherein the first seal and the second seal are formed as a single component.

9. The sealing system of claim 7, wherein at least one of the first and second seals is comprised of an elastomeric material.

10. The sealing system of claim 7, wherein at least one of the first and second seals is comprised of a polymeric material.

11. The sealing system of claim 7, wherein the second seal is at least partially positioned within a groove defined in a surface of a gas analyzer.

12. The sealing system of claim 7, wherein the sealing chamber is fluidly coupled to the vacuum chamber using one or more conduits that are formed as part of a gas analyzer.

13. A method of sealing a junction between a valve and a vacuum chamber:

structuring a sealing system to comprise, a first seal positioned at an interface between the valve and a housing of the vacuum chamber, a second seal spaced apart from the first seal and positioned at the interface between the valve and the housing of a vacuum chamber, wherein the valve includes an inlet and an outlet and the second sealing member surrounds the inlet and the outlet of the valve, and a sealing chamber defined between the first and second seals;

fluidly connecting the sealing chamber to the vacuum chamber;

maintaining the sealing chamber at a pressure that is below atmospheric pressure when in operation; and removing contaminants that breach one of the first and second seals, wherein the two components comprise a valve and a vacuum chamber, and wherein the sealing chamber is fluidly connected to an interior of the vacuum chamber.

14. The method of claim 13, further comprising structuring at least one of the first and second seals to comprise an elastomeric material.

15. The method of claim 13, further comprising at least partially positioning the second seal within a groove defined in a surface of a gas analyzer.

16. The method of claim 13, wherein fluidly connecting the sealing chamber to the vacuum chamber includes one or more conduits that are formed as part of a gas analyzer.

17. The sealing system of claim 1, wherein the vacuum chamber is fluidly connected to a vacuum pump, and wherein the sealing chamber is pumped down as the vacuum chamber is pumped down by the vacuum pump.

18. The sealing system of claim 7, wherein the vacuum chamber is fluidly connected to a vacuum pump, and wherein the sealing chamber is pumped down as the vacuum chamber is pumped down by the vacuum pump.

19. The sealing system of claim 1, wherein the outer sealing member is configured to extend around the inner sealing member.

20. The sealing system of claim 7, wherein the first seal is configured to extend around the second seal.

* * * * *